United States Patent [19]

Hrushesky

[11] Patent Number: 4,930,518

[45] Date of Patent: Jun. 5, 1990

[54] SINUS ARRHYTHMIA MONITOR

[76] Inventor: William J. M. Hrushesky, 3123 James Ave. South, Minneapolis, Minn. 55408

[21] Appl. No.: 248,588

[22] Filed: Sep. 26, 1988

[51] Int. Cl.$^5$ ............................................ A61B 5/205
[52] U.S. Cl. .................................................. 128/671
[58] Field of Search .............. 128/671, 670, 700, 702, 128/695, 696, 716, 725, 687, 28

[56] References Cited

U.S. PATENT DOCUMENTS

| | | | |
|---|---|---|---|
| 3,572,317 | 3/1971 | Wade | 128/696 |
| 3,675,640 | 7/1972 | Gatts | 128/671 |
| 4,031,884 | 6/1977 | Henzel | 128/671 |
| 4,036,211 | 7/1977 | Veth et al. | 128/671 |
| 4,368,740 | 1/1983 | Binder | 128/725 |
| 4,463,764 | 8/1984 | Anderson et al. | 128/671 |
| 4,510,944 | 4/1985 | Porges | 128/687 |
| 4,519,395 | 5/1985 | Hrushesky | 128/671 |

FOREIGN PATENT DOCUMENTS

| | | | |
|---|---|---|---|
| 0158648 | 9/1963 | U.S.S.R. | 128/671 |
| 0167604 | 1/1965 | U.S.S.R. | 128/700 |
| 1169608 | 7/1985 | U.S.S.R. | 128/696 |

OTHER PUBLICATIONS

Akselrod, S., et al., "Power Spectrum Analysis of Heart Rate Fluctuation," Science, 213:220-222, 1981.
Williams et al., "Interrelationships of Cardiac Output, Blood Pressure, and Peripheral Resistance during Normal Respiration in Normotensive and Hypertensive Individuals," Circulation 4:278-286, 1951.
Flaherty et al., "Influence of Respiration on Recording Cardiac Potentials," American Journal of Cardiology, 20:21-28, 1967.
Lauson et al., "The Influence of Respiration on the Circulation in Man," American Journal of Medicine, vol. 1, 10-1946, 315-336.
Melcher, "Respiratory Sinus Arrhythmia in Man," Acta Physiologica Scandinavica, 435:6-25, 1976.
Almasi et al., "Basic Technology of Voluntary Cardiorespiratory Synchronization in Electrocardiology," IEEE BioMed. Engr., 21: 7-1974.

Primary Examiner—Lee S. Cohen
Assistant Examiner—Kennedy J. Schoetzle
Attorney, Agent, or Firm—Kinney & Lange

[57] ABSTRACT

An instrument for measuring physiological characteristics of a living organism based upon the monitoring of the respiratory sinus arrhythmia senses a subject's heartbeat and senses beginning of inspiration and expiration in the subject's respiratory cycles. Instantaneous heart rate values are derived for each heartbeat. A time value is stored for each heartbeat, and from those time values the temporal location of each instantaneous heart rate within the respiratory cycle of the patient is determined. Based upon the time values and the instantaneous heart rate values corresponding to those time values, measurement values which indicate a characteristic of the subject's cardiovascular and/or cardiopulmonary systems are derived. Corrections for the effects of mean heart rate, respiratory rate, respiratory volume and respiratory flow rate, and time of day of the test, are provided.

43 Claims, 3 Drawing Sheets

SINUS ARRHYTHMIA MONITOR

BACKGROUND OF THE INVENTION

1. Field of the Invention

The present invention relates to an apparatus and method for measurement of a physiologic function. In particular, the present invention relates to a noninvasive medical instrument for noninvasive measurement of physiologic characteristics based upon the monitoring of heartbeats and respiratory cycle in order to determine quantitatively the respiratory sinus arrhythmia (RSA).

2. Description of the Prior Art

In my U.S. Pat. No. 4,519,395 entitled "Medical Instrument for Noninvasive Measurement of Cardiovascular Characteristics", which issued May 28, 1985, I described an apparatus and method which provided a precise and highly reproducible quantitative measurement of sinus arrhythmia. The apparatus described in my U.S. Pat. No. 4,519,395 uses a pulse transducer to provide signal pulses representative of sensed heartbeats of the human subject. Stimuli are provided to the human subject as a function of the signal pulses in order to permit the human subject to voluntarily synchronize the subject's respiratory cycles with the heartbeats. In this way, each respiratory cycle corresponds to a predetermined number of heartbeats.

The apparatus described in my U.S. Pat. No. 4,519,395 determines instantaneous heart rate for each beat of the end beat voluntarily synchronized respiratory cycles based upon the time interval between signal pulses and sorts the instantaneous heart rate data by beat. A digital computer analyzes the sorted digital data and derives one or more digital values which are indicative of a characteristic of the subject's cardiovascular system. This data analysis preferably includes rhythmometric, statistical, and arithmetic analyses based upon the sorted digital data.

Using the apparatus of my U.S. Pat. No. 4,519,395, it is possible to provide a highly sensitive quantitative measurement of sinus arrhythmia parameters. As described in my patent, these parameters provide information which is useful in the quantification of physiologic cardiovascular age. The effects of toxins, cardiac drugs, hormones and aerobic exercise (or other forms of cardiovascular training) and the status of various cardiovascular or pulmonary disease states can also be monitored using this medical instrument.

SUMMARY OF THE INVENTION

The present invention is an improvement to my previous sinus arrhythmia monitor which eliminates the need for voluntary synchronization of the subject's respiratory cycles to the subject's heartbeats. With the present invention, therefore, the test is simpler to administer and to take, and permits testing of children and others who are unable to follow visual or auditory commands, experimental animals, and comatose patients.

With the present invention, heartbeats of the subject and breathing cycles of the subject are sensed. An instantaneous heart rate value is determined for each sensed heartbeat and that value is located within the respiratory cycle based upon the temporal relationship between the sensed breathing cycles and the sensed heartbeat. Using the instantaneous heart rate values and the time values indicating location within the breathing cycle, digital values indicative of characteristics of the subject's cardiovascular and cardiopulmonary systems are derived.

In further embodiments of the present invention, values representative of mean heart rate, respiratory rate, respiratory volume and average rates of air flow during inspiration and expiration are derived from input signals. These values, along with the time of day of the test, are then used to correct (or normalize) the sinus arrhythmia values (such as amplitude) which have been derived to eliminate these sources of inter-test variability.

In the preferred embodiment, derived sinus arrhythmia values from each subject are stored and compared to each previous value for that subject and to those obtained from a large group of normal subjects of the same and other ages. Nomograms derived from tests of several thousand subjects serve as a reference to aid interpretation of single and serial test values from the individual subjects. Numerical data and graphic outputs are provided which make each test value fully interpretable at a glance.

DETAILED DESCRIPTION OF THE PREFERRED EMBODIMENTS

In the present invention, instantaneous heartbeat information and breathing information are analyzed using cosinor rhythmometric analysis and other analytic methods to provide an instantaneous, precise and highly reproducible assessment of sinus arrhythmia amplitude and phase (timing of peak) relative to the beginning of inspiration. This sinus arrhythmia amplitude and phase, along with other parameters of cardiovascular performance obtained using the present invention, are useful in a wide variety of applications in medical practice, public health, health care maintenance and exercise physiology, and measurements of aerobic training effect.

Figure 1:
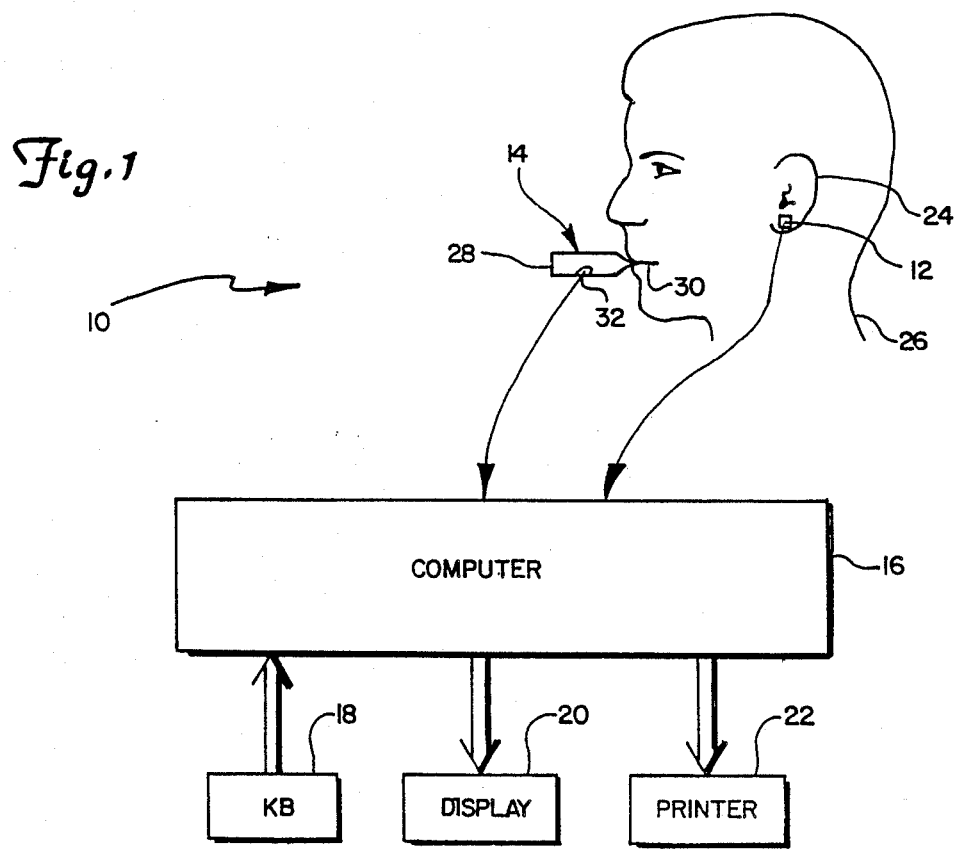
FIG. 1 is a block diagram of a preferred embodiment of the system of the present invention.

FIG. 1 shows a block diagram of sinus arrhythmia testing instrument 10 which includes heartbeat sensor 12, breathing sensor 14, microcomputer 16, keyboard 18, display 20 and printer 22. In the embodiment shown in FIG. 1, heartbeat sensor 12 is a photoelectric pulse sensor which is attached to ear lobe 24 of patient or subject 26. The signal from heartbeat sensor 12 is received by interface circuitry within microcomputer 16 and provides an interrupt heartbeat signal to microcomputer 16 each time a heartbeat is sensed.

Breathing sensor 14 includes a mouthpiece 28 which is placed in mouth 30 of patient 26. Temperature sensor 32, which is preferably a thermistor, is positioned within mouthpiece 28 and provides a signal which is a function of temperature change of air passing through mouthpiece 28. In general, the air being drawn in through mouthpiece 28 during inspiration is cooler than the air being exhausted through mouthpiece 28 during expiration. By monitoring the temperature changes represented by the signal from temperature sensor 32, and exhale interrupt signal and an inhale interrupt signal are generated. The inhale interrupt signal is produced at the beginning of each inspiration or inhalation portion of the breathing cycle. It is sensed by the fall in air temperature associated with pulling room temperature air through mouthpiece 28 past temperature sensor 32 and into subject 26. The end of the inhalation or inspiration component of the respiratory cycle and the concurrent beginning of the exhalation or expiration component of the cycle is sensed when the warmer body temperature expired air passes through mouthpiece 28. This rise in air temperature causes the exhale interrupt signal to be produced. It is understood, of course, that any alternative methods of pulse and respiratory sensing could be substituted for those depicted in FIG. 1 and described above.

Microcomputer 16 includes a real time clock with which the timing of the inhale interrupt signal, the exhale interrupt signal, and each heartbeat interrupt signal can be determined. Instantaneous heart rate is calculated by microcomputer 16 for each heartbeat by measuring the time interval between each heartbeat interrupt signals and the preceding heartbeat interrupt signal. Microcomputer 16 places each instantaneous heart rate at its proper position in the breathing cycle, in either the inspiration or expiration portion of that cycle. The same rhythmometric and statistical analyses are then applied to the instantaneous heart rate values, placed in proper position in the breathing cycle, which were performed in my U.S. Pat. No. 4,519,395, and that description is incorporated by reference. It is understood, of course, that other forms of analyses can also be used in accordance with the present invention.

Using the system of the present invention, the number of heart beats during a breathing cycle is not necessarily identical or predetermined. The subject no longer is required to breathe at any set multiple of the pulse rate, and need not follow any special computer-directed synchronizing instructions.

This has several important advantages. First, the present invention makes the test much simpler both to administer and to take. Three to ten normal breaths furnish adequate data for a reliable analysis and interpretation.

Second, the present invention allows data collection from children, elderly or unconscious individuals and others who are unable to follow the commands necessary for cardiorespiratory synchronization. The testing is also more "natural" because the subject simply breathes at his or her own natural respiration rate and volume.

Third, the present invention markedly diminishes or eliminates test-to-test and subject-to-subject variability, which stems from the varying ability within and between subjects to obey accurately the breathing commands required for voluntary cardiorespiratory synchronization.

Using voluntary cardiorespiratory synchronization of the type described in my previous U.S. Pat. No. 4,519,395, it was possible for synchronization errors to occur because of errors in the actual breathing response of the subject to the prompting of the voluntary cardiorespiratory synchronization circuit. One respiration cycle could actually contain one too many pulses and another one too few. In addition, the data analysis performed in my previous patent assumed that the beats were equally spaced in time, which is not, in fact, the case. By locating the actual temporal position of each instantaneous heart rate within a respiration cycle, rather than assuming equidistant spacing, a more accurate rhythmometric least squares curve fitting can be performed, and thus the parameters derived from that fitted curve (such as sinus arrhythmia amplitude and peak timing) are more accurately determined.

Fourth, data collected using the present invention fits the analytical model (i.e. a cosine function) chosen to quantify the respiratory sinus arrhythmia much better than data obtained during voluntary cardiorespiratory synchronization.

Figure 2:
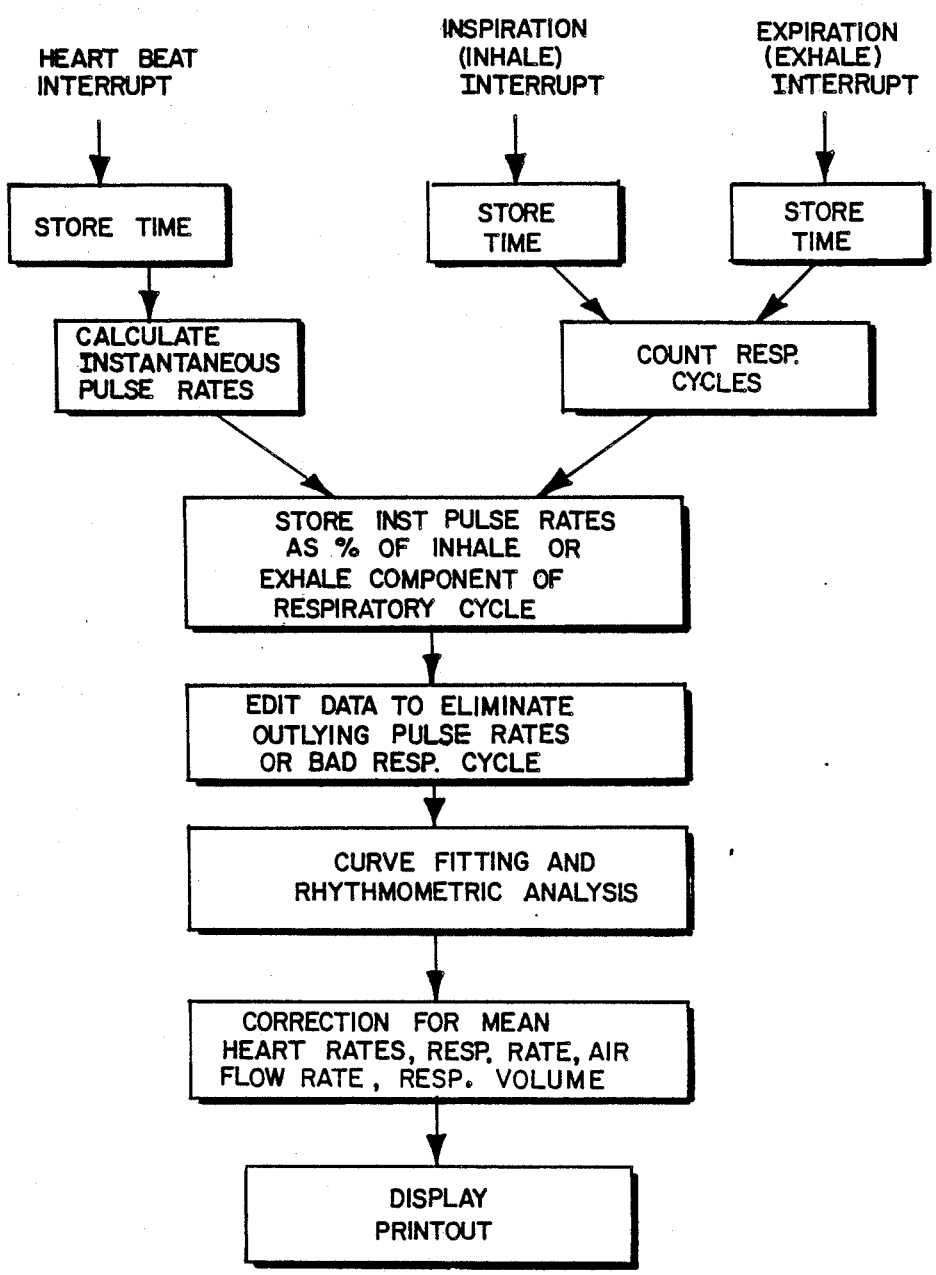
FIG. 2 is a flow chart illustrating operations of the present invention.

FIG. 2 is a flow chart showing the operation of microcomputer 16 in processing data based upon the heartbeat, inhale, and exhale interrupt signals. Each time a heartbeat interrupt signal is received, the time at which the heartbeat occurred is stored. From the stored times, an instantaneous heart rate is calculated and stored for each heartbeat. Each time an inhale interrupt signal is received, the time is stored, and the same is done for each exhale interrupt signal. Based upon the inhale and exhale interrupt signals, microcomputer 16 also counts the respiratory cycles.

Microcomputer 16 then stores the instantaneous pulse rates as a percentage of the respiration cycle. In one preferred embodiment of the present invention, those pulses which occurred between an inspiration interrupt signal and an expiration interrupt signal are placed in the inspiration component of the cycle and are stored as a percentage of elapsed time from the inhale interrupt with respect to the time between the inhale interrupt and the exhale interrupt. Similarly, those pulses which occurred between the exhale interrupt and the next inhale interrupt are placed in the expiration component of the respiration cycle. The instantaneous pulse rates are stored as a percentage of the expiration component of the respiratory cycle (i.e. the elapsed time from the exhale interrupt to the heartbeat interrupt divided by the time from the exhale interrupt to the next inhale interrupt).

Microcomputer 16 then compares the stored data against predetermined criteria in order to eliminate instantaneous heart rates which are clearly out of range or inspiration/expiration cycles which have durations which are outside of a normal range.

Once the editing function has been performed, microcomputer 16 then performs a fitting of the data to a curve. Preferably, this fitting is to a cosine function. Based upon this cosinor analysis, the mesor (rhythm adjusted mean), amplitude (one half of the predictable variation of the fitted curve of pulse around mean pulse value), and acrophase (timing of the peak of the best fitting cosine curve to the pulse data) of the curve, and the statistical quality of the curve fit are derived.

Microcomputer 16 then displays data on display 20 (and can print the data through printer 22). The displayed data can take a number of different forms. In one preferred embodiment of the present invention, the displays include (1) a continuous display, in which raw instantaneous heart rate data are plotted in a continuous fashion over time, by least squares analysis (2) a folded display in which each respiratory cycle is folded on top of previous cycles and displayed, and (3) a means and errors display in which the folded data is averaged within defined regions and displayed as averages with standard error marks.

In each of these display modes, the cosine fit may be indicated, and the individual points of the curve may or may not be interconnected. The displays also can indicate pulse rate in numerical values or as a percent of rhythm adjusted mean (mesor). Standard curves with standard errors and confidence intervals for different age groups may also be displayed as part of these display formats. These standard curves (or nomograms) are based upon data from a large number of normal subjects and are stored by microcomputer 16. A value derived from the relationship of the individual test subject's amplitude to the amplitude expected for his/her age may also be provided as percentage "expected for age". An individual with an amplitude of 2 whose "expected for age value" was 4 would have a value of 2/4×100 or 50% of that expected for his/her age. All previous test results for the individual may be displayed with the new test result. Longitudinal tests from the same individual may be displayed as a function of the test date; and trends in mesor, amplitude or acrophase may be easily visualized using this longitudinal format. Relevant event lives can also be portrayed upon these displays.

Still another method of analysis is a "serial section". Cosine curves are fitted to integral parts of the entire test (for example, on a cycle-by-cycle basis). A display is provided on display 20 which shows the amplitudes and phases of each cosine fit. This allows the user to see, using pattern recognition techniques, the differences between parts of the data in terms of the quality of fit, amplitude, mesor, and phase. This information can be used to recognize any significant changes in the RSA rhythm characteristics from the beginning to the end of the testing span.

It has been discovered that there are several other parameters which affect the sinus arrhythmia and which, in preferred embodiments of the present invention, are used to provide a more accurate and standardized or "normalized" measurement of cardiovascular-cardiopulmonary condition. Specifically, these parameters include the mean heart rate during the test and any trend during the test, the mean respiratory rate, the respiratory volume and means airflow rates during each phase of the respiratory cycle.

In general, the higher the mean heart rate, the lower the sinus arrhythmia amplitude around that mean heart rate. The sinus arrhythmia amplitude decreases somewhat with increasing respiratory rate. Finally, as respiratory volume increases, sinus arrhythmia amplitude increases. Air flow rate changes predictably as a function of both respiratory rate and volume as well as independently as a function of respiratory condition.

These four parameters, of course, are not totally independent of one another. As respiratory rate increases, there is less time in which to inhale and exhale, and respiratory volume will generally tend to decrease and air flow rate will increase.

Figure 3A:
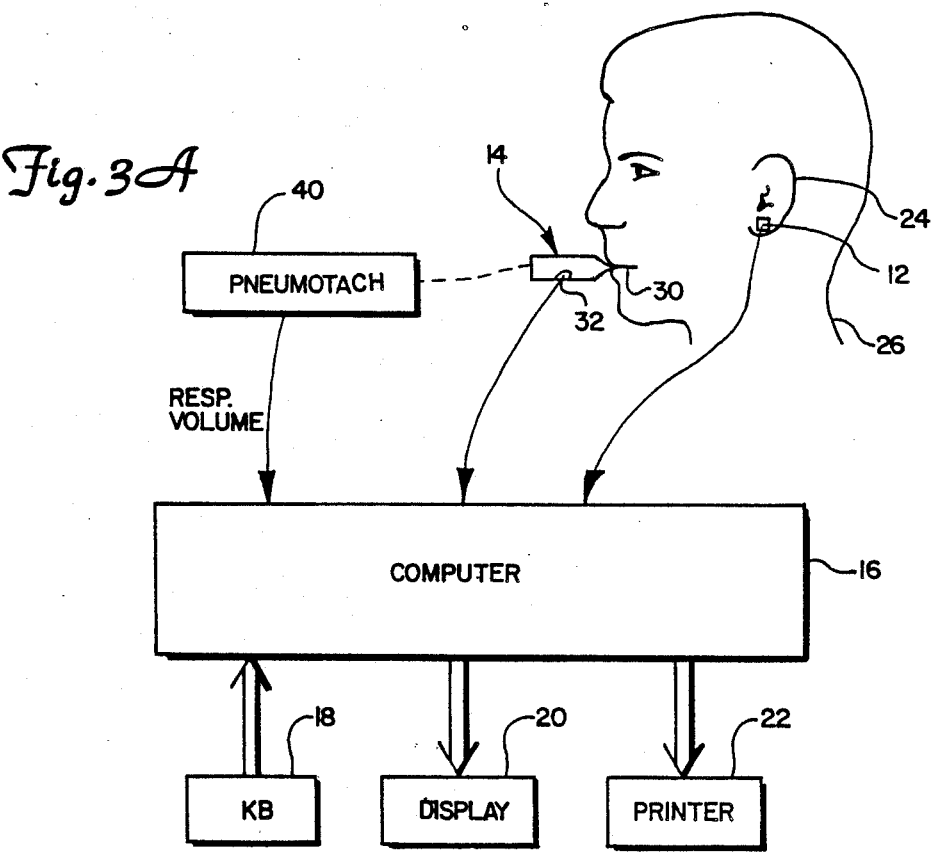
FIGS. 3A and 3B are block diagrams of additional preferred embodiments of the present invention.
Figure 3B:
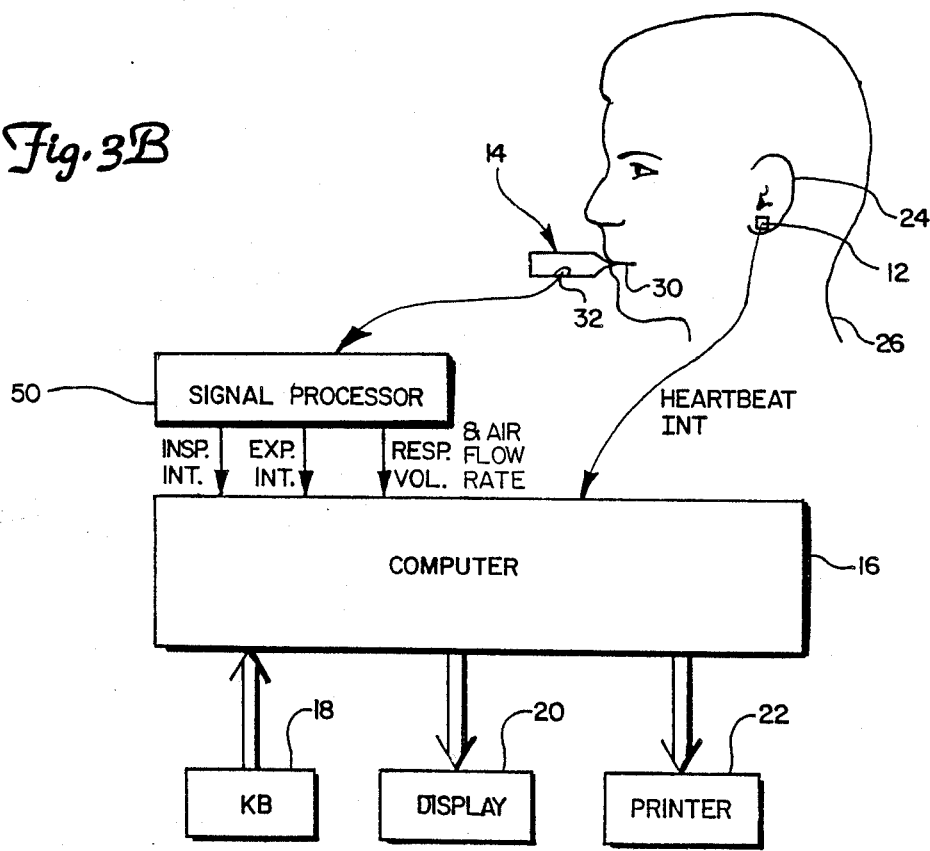

The mean heart rate and the respiratory rate are known by microcomputer 16 based upon the signals from sensors 12 and 32. The respiratory volume and air flow rates, however, require an additional signal which either indicates the respiratory volume directly or which can be used, together with other stored data, to calculate a respiratory volume. In the embodiment of the present invention shown in FIG. 3A, pneumotachometer 40 is connected to mouthpiece 28 and provides a respiratory volume and air flow rate signals to microcomputer 16. In the embodiment shown in FIG. 3B, the temperature signal from temperature sensor 32 in mouthpiece 28 is supplied to respiration signal processing circuit 50. The outputs of circuit 40 include inspire and expire interrupt signals and a dT/dt signal representative of rate of change of temperature across temperature sensor 32. This rate of change of temperature signal is correlated by microcomputer 16 with stored data representative of the volume of the mouthpiece in order to calculate the volume of air moving into or out of subject 26 through mouthpiece 28 and its flow rate during inspiration and expiration.

Based upon the respiratory rate, the heart rate and the respiratory volume and average air flow rates, microcomputer 16 provides corrections to the other derived values such as sinus arrhythmia amplitude. In this way, four sources of base line variability in the sinus arrhythmia can be corrected for or used to sort the results from various subjects so that a meaningful comparison of data from subject to subject or longitudinally in the same subject can be made.

For example, such corrections for inter-test variability may be important when subjects are measured at different times (i.e. a longitudinal study of the same subject) to determine whether the changes in sinus arrhythmia amplitude are due to a physiologic difference in the heart or lungs as opposed to merely a higher mean heart rate at the time of one test versus another.

Any effect of a trend in heart rate during a test or even between tests can also be minimized by analyzing the heart rate as percent of the mesor (rhythm adjusted mean) during that test.

Still another factor which can result in inter-test variability (even with the same subject) is the time of day when the test is performed. In preferred embodiments, microcomputer 16 includes a real time clock to determine the time of day of each test. Corrections for known variations in test performance based on the time of day are made to the values derived by microcomputer 16.

In conclusion, the present invention represents significant improvements to my earlier developed medical instrument for measurement of cardiovascular-cardiopulmonary characteristics based upon the respiratory sinus arrhythmia. With the present invention, the tests are easier to perform, can be used upon additional subjects who may not have the ability to comply with visual or auditory signals instructing them when to breathe, and are more accurate. In addition, the present invention is capable of miniaturization, so that it is portable (preferably the size of a cigarette package) and can be carried by the physician or carried or worn by the subject.

Although the present invention has been described with reference to preferred embodiments, workers skilled in the art will recognize that changes may be made in form and detail without departing from the spirit and scope of the invention.

What is claimed is:

1. In an apparatus for measuring sinus arrhythmia of a subject, the improvement comprising:
   means for determining respiratory volume;
   means for determining respiratory rate;
   means for determining mean heart rate;
   means for correcting a measurement of sinus arrhythmia as a function of respiratory volume, respiratory rate and mean heart rate.

2. The improvement of claim 1 and further comprising:
   means for determining average air flow rate during respiration; and
   means for correcting the measurement of sinus arrhythmia as a function of average air flow rate.

3. In an apparatus for measuring sinus arrhythmia of a subject based upon sensing of heart beats and determination of instantaneous heart rates corresponding to those heart beats, the improvement comprising:

means for sensing beginnings of inhale and exhale components of breathing cycles of the subjects;

means for temporally locating the instantaneous heart rates within the inhale and exhale components of breathing cycles based upon temporal relationships between sensed heart beats and sensed beginnings of inhale and exhale components; and means for deriving a measurement of sinus arrhythmia based upon the instantaneous heart rates and their corresponding temporal locations within the breathing cycles.

4. The invention of claim 3 wherein the means for temporally locating includes:

means for determining whether the instantaneous heart rate is located within an inhale or an exhale component of a sensed breathing cycle; and means for locating the instantaneous heart rate as a percentage of time within that component.

5. The invention of claim 3 and further comprising:

means for determining a respiratory rate based upon the breathing cycles sensed; and means for correcting the measurement of sinus arrhythmia for effects of respiratory rate.

6. The invention of claim 3 and further comprising:

means for determining a mean heart rate of the subject; and means for correcting the measurement of sinus arrhythmia for effects of mean heart rate.

7. The invention of claim 3 and further comprising:

means for sensing respiratory volume; and means for correcting the measurement of sinus arrhythmia for effects of respiratory volume.

8. The invention of claim 3 and further comprising:

means for determining rate of air flow during inspiration and expiration; and means for correcting the measurement of sinus arrhythmia for effects of the rate of air flow.

9. The invention of claim 3 and further comprising;

means for determining a time of day when the measurement of sinus arrhythmia is performed; and means for correcting the measurement of sinus arrhythmia for effects of the time of day.

10. A method of measuring physiologic characteristics of a subject, the method comprising:

sensing changes of direction of respiratory flow of the subject to produce inspiration and expiration signals;

sensing heart beats of the subject to produce heart beat signals;

determining an instantaneous heart rate for each heart beat;

determining temporal locations of the instantaneous heart rates within respiratory cycles based upon temporal relationships between the inspiration and expiration signals and the heart beat signals; and deriving a measured physiological characteristic based upon the instantaneous heart rates and their corresponding temporal locations.

11. The method of claim 10 wherein deriving a measured characteristic includes:

deriving a curve which best fits the instantaneous heart rates and their corresponding temporal locations; and deriving rhythm parameters from the curve.

12. The method of claim 11 wherein the rhythm parameters include a sinus arrhythmia amplitude.

13. The method of claim 11 wherein the rhythm parameters include a timing value representative of location at a peak of the curve which best fits.

14. The method of claim 10 and further comprising:

sensing respiratory volume; and correcting the measured characteristics for effects of respiratory volume on sinus arrhythmia.

15. The method of claim 10 and further comprising:

determining a respiratory rate based upon the inspiration and expiration signals; and correcting the measured characteristics for effects of respiratory rate on sinus arrhythmia.

16. The method of claim 10 and further comprising:

determining a mean heart rate based upon the heart beat signals; and correcting the measured characteristic for effects of mean heart rate on sinus arrhythmia.

17. The method of claim 10 and further comprising:

sensing respiratory volume;

determining a respiratory rate based upon the inspiration and expiration signals;

determining a mean heart rate based upon the heart beat signals; and correcting the measured characteristics as a function of respiratory volume, respiratory rate and mean heart rate.

18. The method of claim 10 and furher comprising:

sensing air flow rate during inspiration and expiration; and correcting the measured characteristics for effects of air flow rate on sinus arrhythmia.

19. The method of claim 10 wherein determining temporal locations includes:

determining whether the instantaneous heart rate is located within an inhale or an exhale component of a respiratory cycle; and locating the instantaneous heart rate within the component determined.

20. The method of claim 10 and further comprising:

determining time of day when sensing changes and sensing heart beats takes place; and correcting the measured characteristic for effects of time of day on sinus arrhythmia.

21. The method of claim 10 and further comprising:

storing data representing a nomogram of test results from a plurality of subjects;

displaying the nomogram to permit comparision of the measured characteristic with the nomogram.

22. The method of claim 10 and further comprising:

providing an output presented as the test results from the subject as related to that expected for the subject's age.

23. The method of claim 10 and further comprising:

storing test results of previous tests of the subject using the method; and displaying the test results of the previous tests and the measured characteristics to permit a comparision.

24. In an apparatus for measuring sinus arrhythmia of a subject based upon sensing of heart beats and determination of instantaneous heart rates corresponding to those heart beats, the improvement comprising:

means for sensing breathing cycles of the subject;

means for determining whether the instantaneous heart rate is located within an inhale or an exhale component of a sensed breathing cycle; and means for temporally locating the instantaneous heart rate as a percentage of time within that component; and means for deriving a measurement of sinus arrhythmia based upon the instantaneous heart rates and their corresponding temporal locations within the breathing cycles.

25. In an apparatus for measuring sinus arrhythmia of a subject based upon sensing of heart beats and determination of instantaneous heart rates corresponding to those heart beats, the improvement comprising:
   means for sensing breathin cycles of the subject;
   means for temporally locating the instantaneous heart rates within the breathing cycles;
   means for deriving a measurement of sinus arrhythmia based upon the instantaneous heart rates and their corresponding temporal locations within the breathing cycles;
   means for determining a respiratory rate based upon the breathing cycles sensed; and
   means for correcting the measurement of sinus arrhythmia for effects of respiratory rate.

26. In an apparatus for measuring sinus arrhythmia of a subject based upon sensing of heart beats and determination of instantaneous heart rates corresponding to those heart beats, the improvement comprising:
   means for sensing breathing cycles of the subject;
   means for temporally locating the instantaneous heart rates within the breathing cycles;
   means for deriving a measurement of sinus arrhythmia based upon the instantaneous heart rates and their corresponding temporal locations within the breathing cycles;
   means for sensing respiratory volume; and
   means for correcting the measurement of sinus arrhythmia for effects of respiratory volume.

27. In an apparatus for measuring sinus arrhythmia of a subject based upon sensing of heart beats and determination of instantaneous heart rates corresponding to those heart beats, the improvement comprising:
   means for sensing breathing cycles of the subject;
   means for temporally locating the instantaneous heart rates within the breathing cycles;
   means for deriving a measurement of sinus arrhythmia based upon the instantaneous heart rates and their corresponding temporal locations within the breathing cycles;
   means for determining rate of air flow during inspiration and expiration; and
   means for correcting the measurement of sinus arrhythmia for effects of the rate of air flow.

28. In an apparatus for measuring sinus arrhythmia of a subject based upon sensing of heart beats and determination of instantaneous heart rates corresponding to those heart beats, the improvement comprising:
   means for sensing breathing cycles of the subject;
   means for temporally locating the instantaneous heart rates within the breathing cycles;
   means for deriving a measurement of sinus arrhythmia based upon the instantaneous heart rates and their corresponding temporal locations within the breathing cycles;
   means for determining a time of day when the measurement of sinus arrhythmia is performed; and
   means for correcting the measurement of sinus arrhythmia for effects of the time of day.

29. An apparatus for noninvasive quantitative measurement of physiologic characteristics of a living subject, the apparatus comprising:
   means for providing first signals representative of sensed heart beats of the subject;
   means for sensing breathing cycles of the subject and providing second signals representative of beginning of inhale and exhale components of the breathing cycles;
   means responsive to the first signals for providing first digital data representative of instantaneous heart rate of each sensed heart beat;
   means for determining a temporal location of each of the instantaneous heart rates within the breathing cycles based upon temporal relationships of the first and second signals and providing second digital data representative of the temporal location;
   means for analyzing the first and second digital data to derive a digital value indicative of a physiological characteristic of the subject; and
   means for providing a human perceivable output as a function of the derived digital value.

30. The apparatus of claim 29 wherein the means for analyzing includes:
   means for deriving a mathematical function which best and most qualitatively portrays a relationship of the first and second digital data; and
   means for deriving the digital value from the mathematical function.

31. The apparatus of claim 30 wherein the digital value is representative of sinus arrhythmia amplitude.

32. The apparatus of claim 30 wherein the mathematical function is a cosine curve and the digital value is representative of location of a peak of the cosine curve.

33. The apparatus of claim 29 and further comprising:
   means for providing a third signal representative of respiratory volume;
   means for providing a fourth signal representative of air flow rates during inspiration and expiration;
   means for deriving a mean heart rate value from the first signal;
   means for deriving a respiratory rate value from the second signals; and
   means for correcting the digital value as a function of the respiratory volume, the mean heart rate, the respiratory rate and air flow rate.

34. The apparatus of claim 29 and further comprising:
   means for providing a third signal representative of respiratory volume; and
   means for correcting the digital value for effects of respiratory volume on sinus arrhythmia.

35. The apparatus of claim 29 and further comprising:
   means for providing a signal representative of average air flow rate during inspiration and expiration; and
   means for correcting the digital value for effects of average air flow rate on sinus arrhythmia.

36. The apparatus of claim 29 and further comprising:
   means for providing a mean heart rate based upon the first signals; and
   means for correcting the digital value for effects of mean heart rate on sinus arrhythmia.

37. The apparatus of claim 29 and further comprising:
   means for providing a respiratory rate value as a function of the second signal; and
   means for correcting the digital value for effects of respiratory rate on sinus arrhythmia.

38. The apparatus of claim 29 and further comprising:

means for providing a time of day value representative of a time of day when the measurement of physiologic characteristics was performed; and means for correcting the digital value for effects of time of day on sinus arrhythmia.

39. The apparatus of claim 29 wherein the second signals include an inspiration signal representative of onset of inhalation and an expiration signal representative of onset of exhalation.

40. The apparatus of claim 39 wherein the means for determining temporal location includes:

means for determining temporal location of instantaneous heart rates for sensed heart beats within an inhale component of a breathing cycle as a function of time from an inspiration signal to the first signal corresponding to the sensed heart beats and time from the inspiration signal to a next expiration signal; and means for determining temporal location of instantaneous heart rates for the sensed heart beats within an exhale component of a breathing cycle as a function of time from an expiration signal to the first signal corresponding to the sensed heart beats and time from the expiration signal to a next inspiration signal.

41. The apparatus of claim 29 and further comprising:

means for storing data representing a nomogram of test results from a plurality of test subjects; and means for displaying the nomogram based upon the stored data to permit comparison of the digital value with digital values produced by testing other subjects.

42. The apparatus of claim 29 and further comprising:

means for reporting data based upon a relationship of the subject's test result compared to that expected for the subject's age.

43. The apparatus of claim 42 and further comprising:

means for storing data representing a nomogram of test results from a plurality of test subjects; and means for displaying the nomogram based upon the stored data to permit comparison of the digital value with digital values produced by testing other subjects.

* * * * *

UNITED STATES PATENT AND TRADEMARK OFFICE
CERTIFICATE OF CORRECTION

PATENT NO. : 4,930,518

DATED : June 5, 1990

INVENTOR(S) : William J.M. Hrushesky

It is certified that error appears in the above-identified patent and that said Letters Patent is hereby corrected as shown below:

Col. 7, line 6, delete "subjects", insert --subject--.

Col. 8, line 29, delete "furher", insert --further--.

Col. 9, line 12, delete "breathin", insert --breathing--.

Signed and Sealed this

Thirty-first Day of March, 1992

Attest:

HARRY F. MANBECK, JR.

*Attesting Officer*     *Commissioner of Patents and Trademarks*